US009087149B2

(12) United States Patent
Galley et al.

(10) Patent No.: US 9,087,149 B2
(45) Date of Patent: Jul. 21, 2015

(54) HANDHELD DIABETES MANAGEMENT DEVICE HAVING TESTING IN PAIRS BLOOD GLUCOSE TEST

(75) Inventors: Paul J. Galley, Cumberland, IN (US); John F. Price, McCordsville, IN (US); Richard W. Wilson, Fortville, IN (US); Lisa McCool, Newburgh, IN (US)

(73) Assignee: ROCHE DIAGNOSTICS OPERATIONS, INC., Indianapolis, IN (US)

( * ) Notice: Subject to any disclaimer, the term of this patent is extended or adjusted under 35 U.S.C. 154(b) by 1315 days.

(21) Appl. No.: 12/905,420

(22) Filed: Oct. 15, 2010

(65) Prior Publication Data

US 2012/0095691 A1 Apr. 19, 2012

(51) Int. Cl.
*G01N 33/48* (2006.01)
*G06F 19/00* (2011.01)

(52) U.S. Cl.
CPC .................................. *G06F 19/3462* (2013.01)

(58) Field of Classification Search
CPC .................. G01N 33/48–33/49; G01N 33/66; G06F 19/00; G06F 19/3418; G06F 19/345; G06F 17/306; A61B 5/14532; A61B 5/00; A61M 2230/201; A61M 2202/0486
USPC ............. 702/19, 22, 108, 122–123, 127, 183, 702/187, 189; 600/300, 309, 347, 365; 514/6.7–6.9
See application file for complete search history.

(56) References Cited

U.S. PATENT DOCUMENTS

| 5,019,974 | A  | * | 5/1991  | Beckers .................... 600/316 |
| 6,379,301 | B1 | * | 4/2002  | Worthington et al. ........ 600/309 |
| 7,291,107 | B2 |   | 11/2007 | Hellwig et al. ............... 600/365 |
| 7,553,281 | B2 |   | 6/2009  | Hellwig et al. ............... 600/365 |
| 2004/0172284 | A1 |   | 9/2004 | Sullivan et al. .................... 705/2 |
| 2006/0047192 | A1 |   | 3/2006 | Hellwig et al. ............... 600/365 |
| 2006/0137695 | A1 |   | 6/2006 | Hellwig et al. ............... 128/898 |
| 2008/0058628 | A1 |   | 3/2008 | Hellwig et al. ............... 600/365 |
| 2008/0255707 | A1 | * | 10/2008 | Hebblewhite et al. ........ 700/283 |
| 2010/0069730 | A1 |   | 3/2010 | Bergstrom ..................... 600/365 |
| 2010/0160757 | A1 |   | 6/2010 | Weinert et al. ................ 600/365 |
| 2010/0160759 | A1 |   | 6/2010 | Celentano et al. ............ 600/365 |
| 2010/0168660 | A1 |   | 7/2010 | Galley et al. .................... 604/66 |
| 2010/0212675 | A1 |   | 8/2010 | Walling et al. ................ 128/898 |
| 2010/0218132 | A1 |   | 8/2010 | Soni et al. ...................... 715/771 |
| 2010/0331650 | A1 |   | 12/2010 | Batman et al. ................. 600/365 |

* cited by examiner

*Primary Examiner* — Toan Le
(74) *Attorney, Agent, or Firm* — Harness, Dickey

(57) ABSTRACT

A method for conducting a Testing In Pairs (TIPs) blood glucose (bG) test using a handheld diabetes management device carried by a user. A processing subsystem of the device implements a software module for managing the TIPs test. The software module generates a plurality of predetermined acceptance time windows corresponding to different user defined events. The processing subsystem can identify specific ones of a plurality of bG test values read by the device that are obtained during the predetermined bG acceptance time windows, and which are identified as being related pairs of accepted bG test values that correspond to specific ones of the user defined events. The related pairs of accepted bG test values can then be stored in a database.

19 Claims, 11 Drawing Sheets

FIG. 8

| Event | Reminder | Event Qualifier/Trigger | After Event | Acceptance Window | Reminder |
|---|---|---|---|---|---|
| Breakfast | Brkfst typical time | In acceptance window, meal (+/- 2 h) | PostBreakfast | 1-4 h after meal start, +/- 30 min | 1-4 h after meal time |
| Breakfast | Brkfst typical time | In acceptance window, meal (+/- 2h) | PreLunch | 2 h before typical Lunch to 2 h after typical Lunch | Lunch typical time |
| Lunch | Lunch typical time | In acceptance window, meal (+/- 2 h) | PostLunch | 1-4 h after meal start, +/- 30 min | 1-4 h after meal time |
| Lunch | Lunch typical time | In acceptance window, meal (typical lunch +/- 2h) | PreDinner | 2 h before typical Dinner to 2 h after typical Dinner | Dinner typical time |
| Dinner | Dinner typical time | In acceptance window, meal (typical dinner +/- 2 h) | PostDinner | 1-4 h after meal start, +/- 30 min | 1-4 h after meal time |
| Dinner | Dinner typical time | In acceptance window, meal | Bedtime | 2 h before typical Bedtime to 2 h after typical Bedtime | Typical Bedtime |
| Bedtime | Typical Bedtime | In acceptance window, no meal | PreBreakfast | 2 h before typical Brkfst to 2 h after typical Brkfst | Breakfast typical time |
| Exercise | None | Exercise with bG | User-set After Exercise time | 30 min to 6 h after event, +/- 30 min | After Exercise time |
| High bG | None | Above High bG | User-set After High time | 1-6 h after event, +/- 30 min | After High bG time |
| Low bG | None | Below Low bG | After Low Time | 5 to 30 min after event, +/- 15 min | After Low bG time |

Possible Data Structure for TIPs Data

| Structured Test # | Start Date | Procedure | Status |
|---|---|---|---|
| 001 | 10/01/2010 | TIPs Pre/Post Breakfast | In Progress |
| 002 | 10/02/2010 | 3 Day Profile | Completed |

FIG. 9

| Date/Time | ST # | Group | Sample | bG | ST Complete | bG Record # |
|---|---|---|---|---|---|---|
| 10/01/2010 7:45 | 001 | 1 | 1 | 85 | √ | 102 |
| 10/01/2010 8:30 | 001 | 1 | 2 | 110 | √ | 103 |
| 10/02/2010 7:40 | 001 | 2 | 1 | 76 | √ | 107 |
| 10/02/2010 8:47 | 001 | 2 | 2 | 128 | √ | 108 |

FIG. 10

HANDHELD DIABETES MANAGEMENT DEVICE HAVING TESTING IN PAIRS BLOOD GLUCOSE TEST

FIELD

The present disclosure relates to systems and methods for assisting a user in carrying out blood glucose (bG) tests, and more particularly to systems and methods for assisting a user in collecting a plurality of related pairs of bG test results for the purpose of carrying out a "Testing In Pairs" test that helps the user in better understanding variances in his/her glycemic levels before and after meals and other various events.

BACKGROUND

This section provides background information related to the present disclosure which is not necessarily prior art.

Diabetes mellitus, often referred to as diabetes, is a chronic condition in which a person has elevated blood glucose levels that result from defects in the body's ability to produce and/or use insulin. There are three main types of diabetes. Type 1 diabetes usually strikes children and young adults, and can be autoimmune, genetic, and/or environmental. Type 2 diabetes accounts for 90-95% of diabetes cases and is linked to obesity and physical inactivity. Gestational diabetes is a form of glucose intolerance diagnosed during pregnancy and usually resolves spontaneously after delivery.

In 2009, according to the World Health Organization, at least 220 million people worldwide suffer from diabetes. In 2005, an estimated 1.1 million people died from diabetes. Its incidence is increasing rapidly, and it is estimated that between 2005 and 2030, the number of deaths from diabetes will double. In the United States, nearly 24 million Americans have diabetes with an estimated 25 percent of seniors age 60 and older being affected. The Centers for Disease Control and Prevention forecast that 1 in 3 Americans born after 2000 will develop diabetes during their lifetime. The National Diabetes Information Clearinghouse estimates that diabetes costs $132 billion in the United States alone every year. Without treatment, diabetes can lead to severe complications such as heart disease, stroke, blindness, kidney failure, amputations, and death related to pneumonia and flu.

Management of diabetes is complex as the level of blood glucose entering the bloodstream is dynamic. Variation of insulin that controls the transport of glucose out of the bloodstream also complicates diabetes management. Blood glucose levels are sensitive to diet and exercise, but also can be affected by sleep, stress, smoking, travel, illness, menses, and other psychological and lifestyle factors unique to individual patients. The dynamic nature of blood glucose and insulin, and all other factors affecting blood glucose, often require a person with diabetes to understand ongoing patterns and forecast blood glucose levels (or at least understand the actions that raise or lower glucose in the body). Therefore, therapy in the form of insulin or oral medications, or both, can be timed to maintain blood glucose levels in an appropriate range.

Management of diabetes is often highly intrusive because of the need to consistently obtain reliable diagnostic information, follow prescribed therapy, and manage lifestyle on a daily basis. Daily diagnostic information, such as blood glucose, is typically obtained from a capillary blood sample with a lancing device and is then measured with a handheld blood glucose meter. Interstitial glucose levels can be obtained from a continuous glucose sensor worn on the body. Prescribed therapies can include insulin, oral medications, or both. Insulin can be delivered with a syringe, an insulin pen, an ambulatory infusion pump, or a combination of such devices. With insulin therapy, determining the amount of insulin to be injected can require forecasting meal composition of carbohydrates, fat and proteins along with effects of exercise or other physiologic states. The management of lifestyle factors such as body weight, diet, and exercise can significantly influence the type and effectiveness of a therapy.

Management of diabetes involves large amounts of diagnostic data and prescriptive data that are acquired from medical devices, personal healthcare devices, patient recorded information, healthcare professional tests results, prescribed medications and recorded information. Medical devices including self-monitoring bG meters, continuous glucose monitors, ambulatory insulin infusion pumps, diabetes analysis software, and diabetes device configuration software each of which generates or manages or both large amounts of diagnostic and prescriptive data. Personal healthcare devices include weight scales, pedometers and blood pressure cuffs. Patient recorded information includes information relating to meals, exercise and lifestyle, as well as prescription and non-prescription medications. Healthcare professional biomarker data includes HbA1C, cholesterol, triglycerides, and glucose tolerance. Healthcare professional recorded information includes therapy and other information relating to the patient's treatment.

There is a need for a handheld patient device to aggregate, manipulate, manage, present, and communicate diagnostic data and prescriptive data from medical devices, personal healthcare devices, patient recorded information, biomarker information and recorded information in an efficient manner to improve the care and health of a person with diabetes, so the person with diabetes can lead a full life and reduce the risk of complications from diabetes.

Further to the above, individuals with diabetes often may need to perform a series of paired glucose tests to help understand particular issues with behavior or therapy. This test involves having an individual obtain pairs of bG values before and after various events. For example, an individual can obtain a bG value before a specific meal, for example before lunch, and another bG value within a specified time after the lunch meal. The "before" and "after" bG values form a related "pair" of bG values and can be used as data for a "Testing In Pairs" (TIPs) test. Collecting and reviewing a plurality of related pairs of before/after bG test data for various events throughout the day (e.g., breakfast, lunch, dinner), while considering the type of food that was consumed at each meal, may help give the individual a better idea of how his/her bG levels are affected by certain foods or events, and thus may help the individual to better manage her/his bG levels throughout the day.

The above described TIPs test, however, can be somewhat inconvenient for an individual to carry out manually. The paired bG values need to be manually recorded by the individual such as by writing down the results in a log. This must be done typically for each meal of the day, and then compiled in such a way that the recorded results are able to show the individual how the bG test values changed throughout the day in response to the meals that the individual consumed. Often an external computer may be needed to present the bG test results in a fashion that aids in understanding the test results. Moreover, the individual must be attentive to the time periods during which the "before" and "after" bG test values must be obtained. Missing a "before" meal bG test will prevent the use of an "after" meal bG test result, for the purpose of constructing a "pair" of bG values for the test.

SUMMARY

This section provides a general summary of the disclosure, and is not a comprehensive disclosure of its full scope or all of its features.

In one aspect the present disclosure relates to a method for conducting a Testing In Pairs (TIPs) blood glucose (bG) test using a handheld diabetes management device carried by a user. The method can comprise using a processing subsystem to implement a software module for managing the TIPs test. The software module can control the generation of a plurality of predetermined acceptance time windows corresponding to different user defined events. The processing subsystem can be used to identify specific ones of a plurality of bG test values read by the device which are obtained during the predetermined bG acceptance time windows, and which are identified as being related pairs of accepted bG test values that correspond to specific ones of the user defined events. The processing subsystem can be used to store the related pairs of accepted bG test values in a database. The processing subsystem can conclude the TIPs test when a predetermined number of pairs of accepted bG test values has been stored in the database and can use the stored bG test values in providing results of the TIPs test to the user.

In another aspect the present disclosure relates to a method for conducting a TIPs test using a handheld diabetes management device carried by a user. The method can comprise using a processing subsystem to implement a software module for managing the TIPs test, the software module controlling the generation of a plurality of predetermined bG acceptance time windows corresponding to different user defined events. A color touchscreen display of the device, which is in communication with the processing subsystem, can be used to enable a user to configure the device to implement the predetermined bG acceptance time windows, to mark bG test values read by the device as preprandial or postprandial bG test values, and to display results of the TIPs test. The processing subsystem can also be used to provide a reminder to the user during each one of the predetermined bG acceptance time windows to perform a bG test and to provide a bG test value for the purpose of carrying out the TIPs test. The processing subsystem can also be used to identify specific ones of a plurality of bG test values read by the device, which are labeled as being related pairs of accepted bG test values that correspond to specific ones of the user defined events. The user defined events may include a plurality of "Before" events and a plurality of "After events" selectable by the user. The Before events can include a Breakfast event, a Lunch event, a Dinner event, a Bedtime event, a Low bG event; a High bG event and an Exercise event. The Afterevents are limited by the choice of the Before event. The processing subsystem can also store the related pairs of accepted bG test values in a database and can conclude the TIPs test when a predetermined number of pairs of accepted bG test values have been stored in the database. The processing subsystem can also be used to retrieve and use the accepted bG test values stored in the database and to display the results of the TIPs test to the user.

In still another aspect the present disclosure relates to a handheld diabetes management device for monitoring and recording bG levels of a user. The device can comprise a port for receiving a bG test strip input by a user and a bG analyzer for reading the bG test strip. A software module can be included for conducting a TIPs test using the device. A processing subsystem can be included which is responsive to an output from the bG analyzer and which uses the bG test value provided by the bG analyzer. The processing subsystem can run the software module, with the software module controlling the generation of a plurality of predetermined acceptance time windows corresponding to different user defined events programmed into the software'module by the user. The processing system can further be adapted to identify specific ones of a plurality of bG test values read by the device, which are obtained during the predetermined bG acceptance time windows, as being related pairs of accepted bG test values that correspond to specific ones of the user defined events. A database can be in communication with the processing subsystem for storing the related pairs of accepted bG test values.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The following figures are selected embodiments of the handheld diabetes manager with enhanced data capability and related system embodiments and information.

FIG. 8 is a table of exemplary times for the various events around which bG test pairs can be obtained using the device of FIG. 1;

FIG. 9 is a chart illustrating how a plurality of different structured tests may be recorded in the device of FIG. 1; and FIG. 10 is a chart showing a data structure which can be used to record the results of a TIPs test in the database of FIG. 2.

Corresponding reference numerals indicate corresponding parts throughout the several views of the drawings.

DETAILED DESCRIPTION

Example embodiments will now be described more fully with reference to the accompanying drawings.

Figure 1:
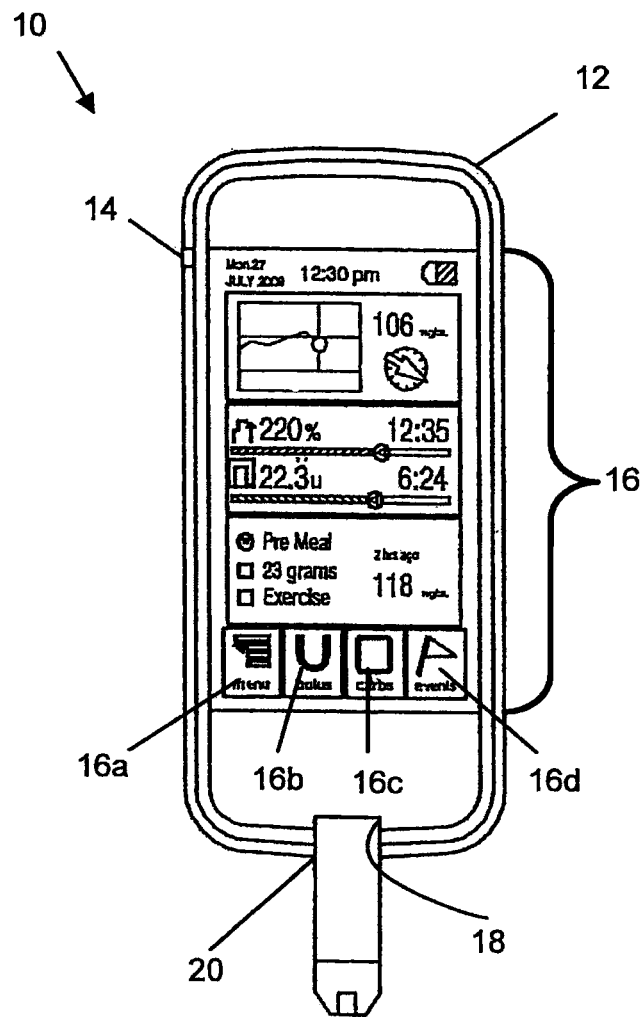
FIG. 1 is a perspective view of one embodiment of a handheld diabetes bG management device in accordance with the present disclosure.

Referring to FIG. 1, there is shown a high level drawing of one embodiment of a handheld, portable blood glucose (bG) monitoring device 10 that can be used in implementing a Testing In Pairs (TIPs) test. Typically the device 10 includes a housing 12 that can contain one or more unit control switches 14 (e.g., ON/OFF), a touchscreen display 16, and a port 18 into which a bG test strip 20 can be inserted. The display 16 can be used in connection with a menu-driven software program that enables a user to access a menu 16a of various selections, such as a selection 16b for allowing the user to enter bolus information, a selection 16c for enabling the user to enter carbohydrate information for snacks or meals, and a selection 16d for allowing the user to enter information pertaining to markers or events (e.g., meals, exercise, periods of stress, etc.) that can affect the user's bG measurement being read by the device 10. Although the display 16 will be described herein as a touchscreen display, it will be appreciated that any other suitable form of display can be incorporated (e.g., LED, etc.). If a touchscreen display is not used, the user control switches 14 may need to include specific buttons or controls by which the user is able to select various options and input markers needed to carry out the TIPs test. It will be appreciated that the above is a high level description of the device 10, and in practice the device can include additional controls, input ports, output ports, etc., as may be desired to even further enhance the utility of the device 10 or its use with other components and devices (e.g., laptop computers, infusion pumps, etc.). Accordingly, the above description of the device 10 should not be taken as limiting its construction or features in any way.

Figure 2:
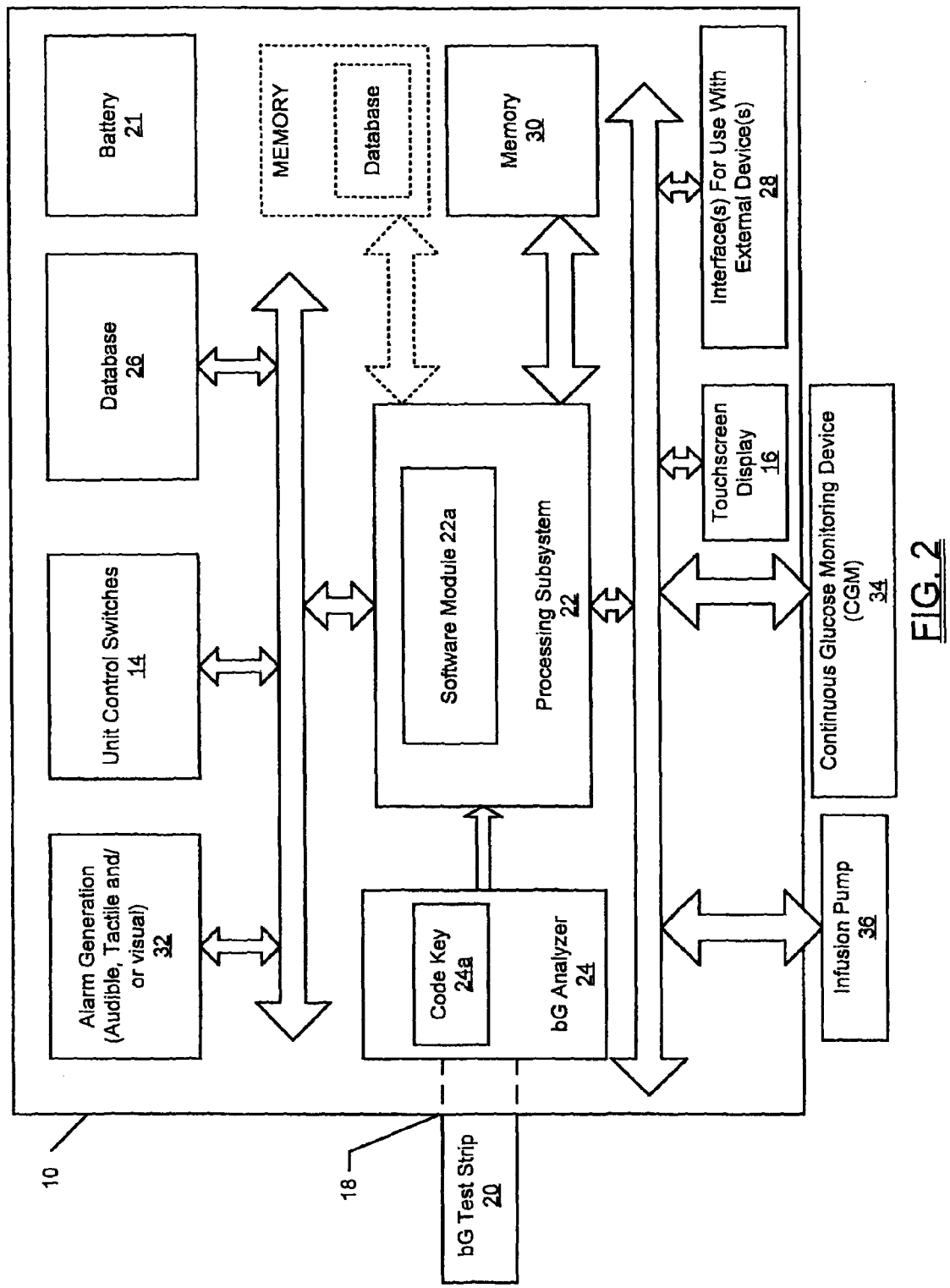
FIG. 2 is a high level block diagram of various components and subsystems that can be incorporated in the device shown in FIG. 1.

Referring to FIG. 2, a high level block diagram of the device 10 is shown. The device 10 can include a rechargeable or non-rechargeable battery 21 for power all the electronic components of the device 10. The device 10 can also include a processing subsystem 22 (e.g., a microprocessor based subsystem) that receives information from a bG analyzer 24. The bG analyzer 24 is in communication with the port 18 of the housing 12 to permit the bG analyzer 24 to read the bG test strip 20. The bG analyzer 24 can include a code key 24a that includes calibration information for the bG test strip 20 being read. The processing subsystem 22 can also be in communication with a database 26, which can be a relational database, that is used to store bG test values obtained from the bG analyzer 24. The processing subsystem 22 can also be in communication with the display 16, the user control panel 14, and one or more interfaces 28 for interfacing the device 10 to other external devices. The processing subsystem 22 can also be in communication with a memory 30 for storing various types of information (e.g., meal times) that are input by the user, as well as any other information requiring temporary or permanent storage. However, it will be appreciated that the database 26 and the memory 30 could be implemented in a single memory device (e.g., RAM) if desired, as indicated in phantom in FIG. 1. The processing subsystem 22 can be in communication with an alarm generation subsystem 32 that can be used to generate reminders to the user consisting of audible signals, tactile signals (e.g., a vibration signal) or even possibly visual signals such as illuminated lights (e.g., LEDs) on the device 10. The processing subsystem 22 can also be in communication with a continuous blood glucose monitoring (CGM) system 34 worn by the user, as well as an insulin infusion pump 36 worn by the user. It will be appreciated that the CGM system 34 and the infusion pump 36 are located remotely from the device 10 and therefore do not form a portion of the device 10.

The device 10 can be used to implement a non-transitory machine readable code, for example a software module 22a, that is run by the processing subsystem 22. The processing subsystem 22, working in connection with the software module 22a, initiates and controls the operation of the TIPs test, and can present the collected TIPs test data obtained in various forms (e.g., charts, graphs, etc.) on the display 16 using one or more colors. The device 10 significantly enhances the convenience and ease to the user in carrying out a TIPs test. Previously, performing a TIPs test has required the user to manually record on a paper chart the bG test information that is obtained before and after meals, and within predetermined acceptance times. By using the device 10, a significant number of highly desirable features can be implemented to remind the user at the appropriate times of the day of the need to obtain and enter bG test values, as well as to organize and segregate the bG test results so that only those bG test results that form the predefined pairs of bG test values are used as related bG pair data for the TIPs results. The device 10 may reduce the likelihood that a user forgets to obtain a bG reading at a required time or otherwise incorrectly manually records bG test data on the paper chart pursuant to performing a TIPs test. The device also eliminates the possibility that the user may forget to carry the paper chart with her/him while travelling during the day, or may not have a writing implement with her/him at the time a bG test result needs to be recorded.

To set up a TIPs test the user can select this option by navigating through various menu items that are displayed and selected through the "Menu" control 16a on touchscreen display 16. The user can select a typical breakfast time, a typical lunch time, a typical dinner time, and a typical bed time, and input these times into the device 10 via the touchscreen display 16. These times can be stored in the memory 30 or alternatively in the database 26. The user can also input a snack "threshold" (e.g., carbohydrate threshold) using the touchscreen display 16, which is also stored in the memory 30 (or possibly the database 26), to distinguish snacks from meals. A bG test result that accompanies a carbohydrate entry that is below the set snack threshold is marked and stored by the processing subsystem 22 as a "Snack" rather than as a "Meal". A carbohydrate entry above the set snack threshold can be marked by the device 10 as a meal. The touchscreen display 16 can also be used to allow the user to enter bG markers (i.e., labels) that designate whether an obtained bG test value is preprandial (i.e., pre-meal) or postprandial (i.e., post-meal).

The software module 22a provides predetermined "acceptance" time windows of varying lengths during which bG test values must be entered by the user for the bG values to be included in the TIPs results. In one embodiment the software module 22a implements acceptance time windows for user provided preprandial bG test values within two hours of the user set meal breakfast, lunch and dinner meal times. The bedtime acceptance time window can be set to within two hours of the user input bedtime. The postprandial acceptance time window can be set to 90-150 minutes after each of the user selected actual meal times. While the above described time windows can be varied through programming modifications to the software module 22a, it is preferred that the user not be able to directly edit or alter the preprandial, bedtime and postprandial acceptance time windows while a test is in progress. Maintaining these predetermined acceptance time windows at the above described durations helps to ensure consistency for pattern recognition. Identification, especially of postprandial excursions, should demonstrate lower glucose variability when the relative measurement time (e.g., 90 to 150 minutes) is enforced. Likewise long-acting insulin is expected to be delivered about the same time every day. Helping to support a more uniform basal insulin dosing time should reduce fasting blood glucose variability.

When the user inserts a bG test trip into the port 18 of the device 10, the bG analyzer 24 reads the test strip and provides a bG test value to the processing subsystem 22. The bG analyzer 24 attaches a bG "time stamp" to the just-obtained bG test value which indicates the time of day that the bG test value was obtained. To assist the user in carrying out the TIPs test, the device 10 can be configured by the user to provide reminders to carry out a bG test during each acceptance time window. The user can optionally be provided with the option to select one of at least three responses to a just-given reminder: "Accept"; "Dismiss"; and "Snooze". It will be understood that the "Accept" and "Dismiss" options could be replaced by a single "OK" or "Close" option with subsequent behavior dependent on the successful completion of a bG test within an acceptance window. In any event, these optional selections may be provided on the display 16 with a check box that the user may select via a touch selection. An "Accept" selection may indicate to the device 10 the user's acknowledgement of the reminder and that the user intends to enter a bG test value within a predetermined number of minutes (e.g., within five minutes). The "Dismiss" selection may allow the user to immediately dismiss the reminder, and all potential follow up reminders, for that particular acceptance time window. The user selecting the "Snooze" option in response to a generated reminder may signal to the processing subsystem 22 to repeat the reminder if the user does not respond to the reminder. The reminder may be repeated within a predetermined time interval, for example within five minutes, for up to a maximum predetermined number of times (e.g., four times maximum), after which the reminder can be automatically dismissed by the processing subsystem 22. If an acceptance time window closes before the maximum number of snooze reminders are generated, then the snooze reminders can be automatically discontinued by the processing subsystem 22 if the user has not responded to any of the reminders. If an acceptance time window closes before the maximum number of Snooze reminders are generated, then the Snooze reminders may be automatically discontinued by the processing subsystem 22. If the Snooze reminder feature is incorporated in the device 10, then it is preferred that Snooze reminders for postprandial acceptance time windows be shorter than those presented for preprandial acceptance time windows. For example, postprandial Snooze reminders may occur every five minutes until the acceptance window is no longer available. Preprandial Snooze reminders may be spaced apart longer, for example every fifteen minutes, until a predetermined maximum number (e.g., four) such reminders have been presented. If the user accepts a given Snooze reminder but then does not enter a bG test value before the next Snooze reminder is scheduled to occur, then the next Snooze reminder may automatically be provided by the processing subsystem 22 as long as the current acceptance time window is open. If the currently open acceptance time window closes before the user has labeled a bG test value that matches the reminder for the acceptance window, then any remaining scheduled reminders are automatically cancelled by the processing subsystem 22.

Figure 3:
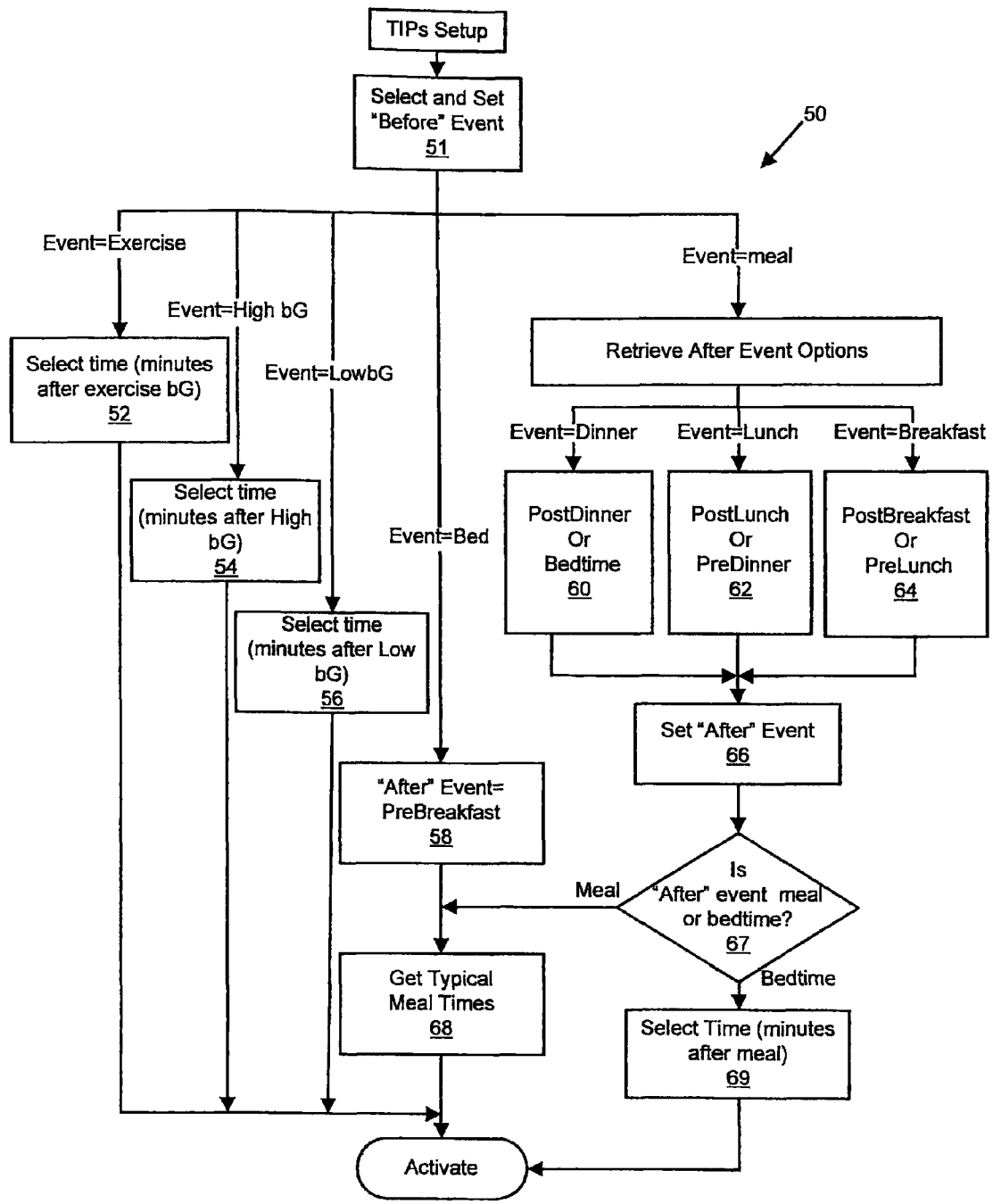
FIG. 3 is an exemplary flowchart of operations that can be performed in setting up a software module of the device to execute a TIPs test.

Referring now to FIG. 3, a flowchart 50 is shown of exemplary operations that can be implemented using the device 10 in configuring the software module 22a of the device to carry out a TIPs test. At operation 51 the user may first select and set a "Before" event. If the Before event is Exercise, initially at operation 52 the user is prompted with a query on the display 16 of the device 10 to select an "After Exercise" time (in minutes) from the exercise bG at which he/she will be prompted to enter an "After Exercise" bG test value during the TIPS test. In one implementation the "After Exercise" time set by the user can vary from thirty minutes to six hours after the user labels the Before Exercise bG test value. The acceptance time window for the user to enter the "After Exercise" bG test value can open thirty minutes before the user selected "After Exercise" time and closes preferably thirty minutes after the user selected "After Exercise" time. However, this acceptance time window could be modified as needed by the system designer, or possibly by even providing additional options to the user in configuring this time window.

If the Before event is High bG, at operation 54 the user also enters on the display 16 a "High bG" time at which an "After" event bG test value can be entered for a "High bG" event. The "High bG" time can be selectable by the user from the display 16 preferably from one hour to six hours after the time stamp for the High bG test value. However, as with the "After Exercise" bG option, this time window could be modified by the system designer. The acceptance window for entering an "After" event bG test value for a "High bG" test result is preferably thirty minutes before the user set "High bG" time to thirty minutes after the user set "High bG" time, although this window could be modified by the system designer to lengthen or shorten it.

If the Before event is Low bG, at operation 56 the user also enters a "Low bG" time at which the user is to be prompted by the device 10 to enter an "After" event bG test value when the user obtains a low bG test value. The "Low bG" time can be five minutes to about thirty minutes after the timestamp for a Low bG test value. The acceptance time window during which the "After" event Low bG test value can be entered can be up to fifteen minutes before the user set "Low bG" time to about fifteen minutes after the user set "Low bG" time. Again, this acceptance time window could be modified by the system designer.

Referring further to FIG. 3, if the event is bedtime, then the "After" event will be a "Pre-breakfast" time (i.e., preprandial time) selected by the user, as indicated at operation 58. This time can be the same as the "Breakfast" time that the user would normally program into the device 10, and can include the same acceptance time window as that provided for the "Breakfast" window. This acceptance time window could be two hours before to two hours after the typical breakfast time.

For a "Dinner" Before event, the "After" event can be selected by the user to be "Post-Dinner" or Bedtime, as indicated at operation 60. The Post-dinner time can preferably be one hour to four hours after the Dinner meal start timestamp, and the acceptance time window can be user set to preferably thirty minutes before the user set Post-meal time to thirty minutes after the user set Post-meal. If the user selects Bedtime as the "After" event, then the acceptance time window will be set according to the user set Bedtime, and will vary, for example, from two hours before the user set Bedtime to two hours after the user set Bedtime.

For a "Lunch Event", the user can select "Post-lunch" or "Pre-dinner as the "After" event, as indicated at operation 62. If the "Post-lunch" option is selected, the acceptance time window and reminders are set in accordance with the postprandial acceptance window, which is preferably centered one to four hours after the Lunch meal timestamp. If the Pre-Dinner option is chosen, then the acceptance window and reminders are chosen according to the time for the next Pre-Dinner acceptance window configured by the user.

For a "Breakfast Event", the user can select either a "Post-Breakfast" or "Pre-Lunch" as the "After" event option, as indicated at operation 64. The acceptance time window for a "Post-breakfast" selection can be, for example, thirty minutes before the user selected Post-meal time to thirty minutes after the user selected Post-meal time. If "Pre-lunch" is selected as the "After" event, then an acceptance time window can be two hours before the user set Pre-lunch time until two hours after the set Pre-lunch time.

The software module 22a then sets the user selected "After" event at operation 66 and then checks to whether the "After" event is a meal or bedtime, or whether the "After" event is a post-meal, as indicated at operation 67. If the "After" event is a meal or bedtime, then the processing subsystem 22 obtains the typical user set meal times, at operation 68. If the "After" event check at operation 67 results in the "After" event being determined to be post-meal, then at operation 69 the user selected time after meal (e.g., one to four hours) is obtained. The software module 22a can then activate the TIPs test when the test is subsequently commanded by the user to start.

Figure 4:
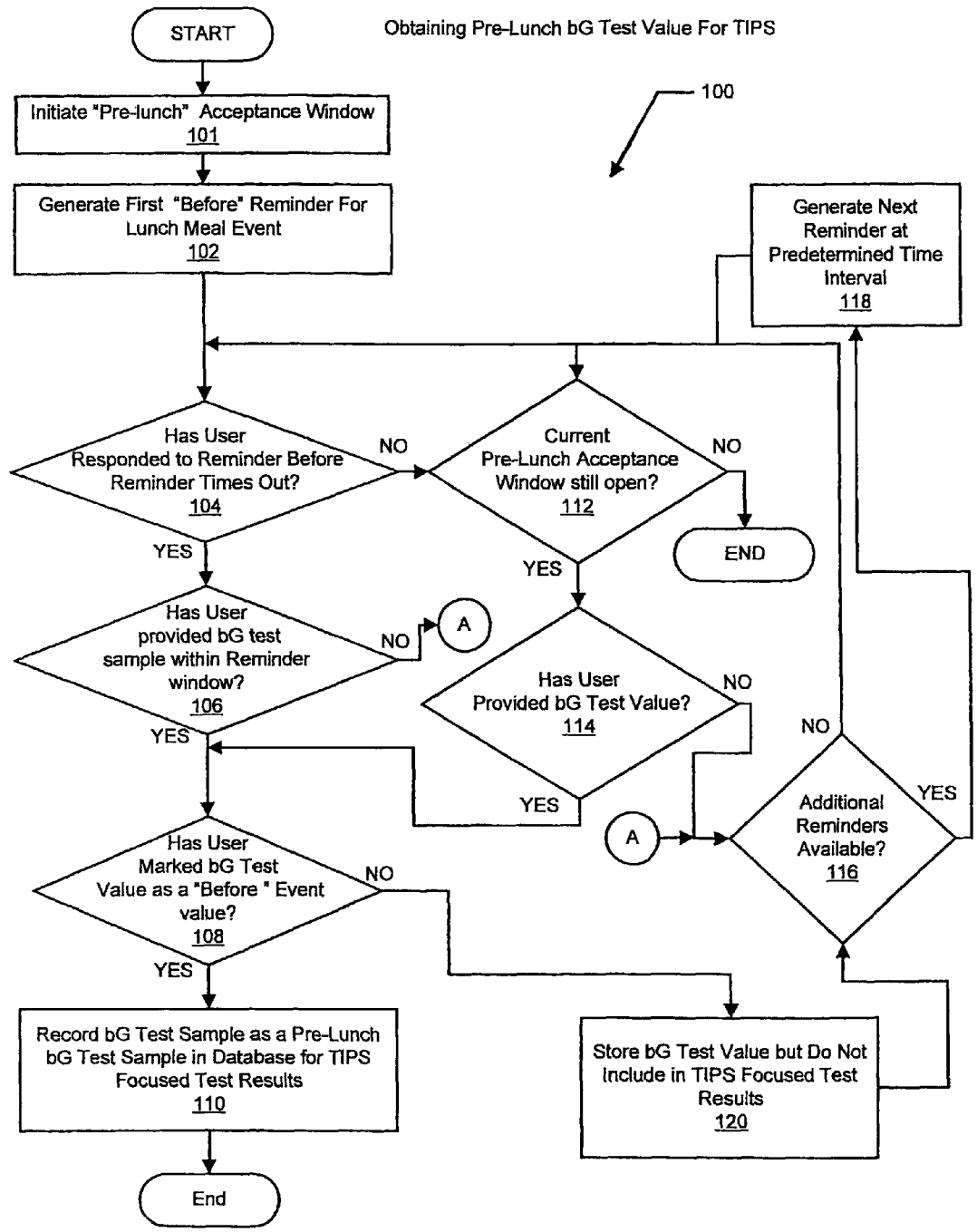
FIG. 4 is an exemplary flowchart of operations that can be performed with the device of FIG. 1 in obtaining a Pre-lunch bG test value from the user.

Referring now to FIG. 4, a flowchart 100 is shown of operations that can be performed using the device 10 and the software module 22a to obtain a Pre-lunch bG test value for the TIPs test. The Pre-lunch meal event acceptance time window is initially opened by the processing subsystem 22, as indicated at operation 101. At operation 102 the device 10 generates the first "Before" reminder for the Lunch meal event. At operation 104 the processing subsystem 22 can check to determine if the user has responded to the reminder before the reminder times out. In this implementation, it will be appreciated that the software module 22a implements a second timer that gives the user a short predetermined time period (e.g., three-five minutes) in which to respond to and accept the reminder, and to perform the requested bG test. If the user accepts the reminder within the short predetermined time period, then at operation 106 the processing subsystem 22 checks to see if the user has entered a time stamped bG test value within the reminder time window. If so, the processing subsystem 22 checks to see if the user has marked (i.e., labeled) the entry as a "Before" event bG entry on the display 16, as indicated at operation 108. If so, then at operation 110 the processing subsystem 22 records the bG test value in the database 26 as a "Before-lunch" bG test value and the Pre-Lunch acceptance window and any pending lunch reminders are closed. If the optional reminder timer is not used, then operations 104 and 106 can be eliminated, and operation 112 would be performed immediately after operation 102. It will also be appreciated that at each opportunity for the user to mark a just-obtained bG test value, the display 16 will display a field where the user may also enter specific notes about the event (e.g., amount of carbohydrates consumed at a given meal). This information will be stored by the processing subsystem 22 together with the related bG test value.

At operation 104, if the user does not accept the reminder before the reminder times out, then at operation 112 the processing subsystem 22 checks to see if the current Pre-lunch acceptance time window is still open. If not, then the user is not permitted to enter a Pre-lunch bG test value for purposes of forming a Lunch Event pair of related bG values for the TIPs test. If the check at operation 112 produces a "Yes" answer, then the processing subsystem 22 checks to determine if the user has provided a time stamped bG test value, as indicated at operation 114. If so, then operation 108 is repeated. If not, then a check is made at operation 116 if additional reminders are available. If so, then the next reminder is generated in accordance with the predetermined time interval (e.g., thirty minutes as in the case of a snoozed reminder), as indicated at operation 118, and operation 104 is repeated. If the check at operation 116 produces a "No" answer, meaning no additional reminders are available, then operation 112 will be repeated.

If the check at operation 108 reveals that the user has not selected the "Before" event (Pre-Lunch) option from the display 16, then at operation 120 the bG test value is stored in the database 26 but is not used for purposes of constructing a related pair of bG test values for the TIN test.

Figure 5:
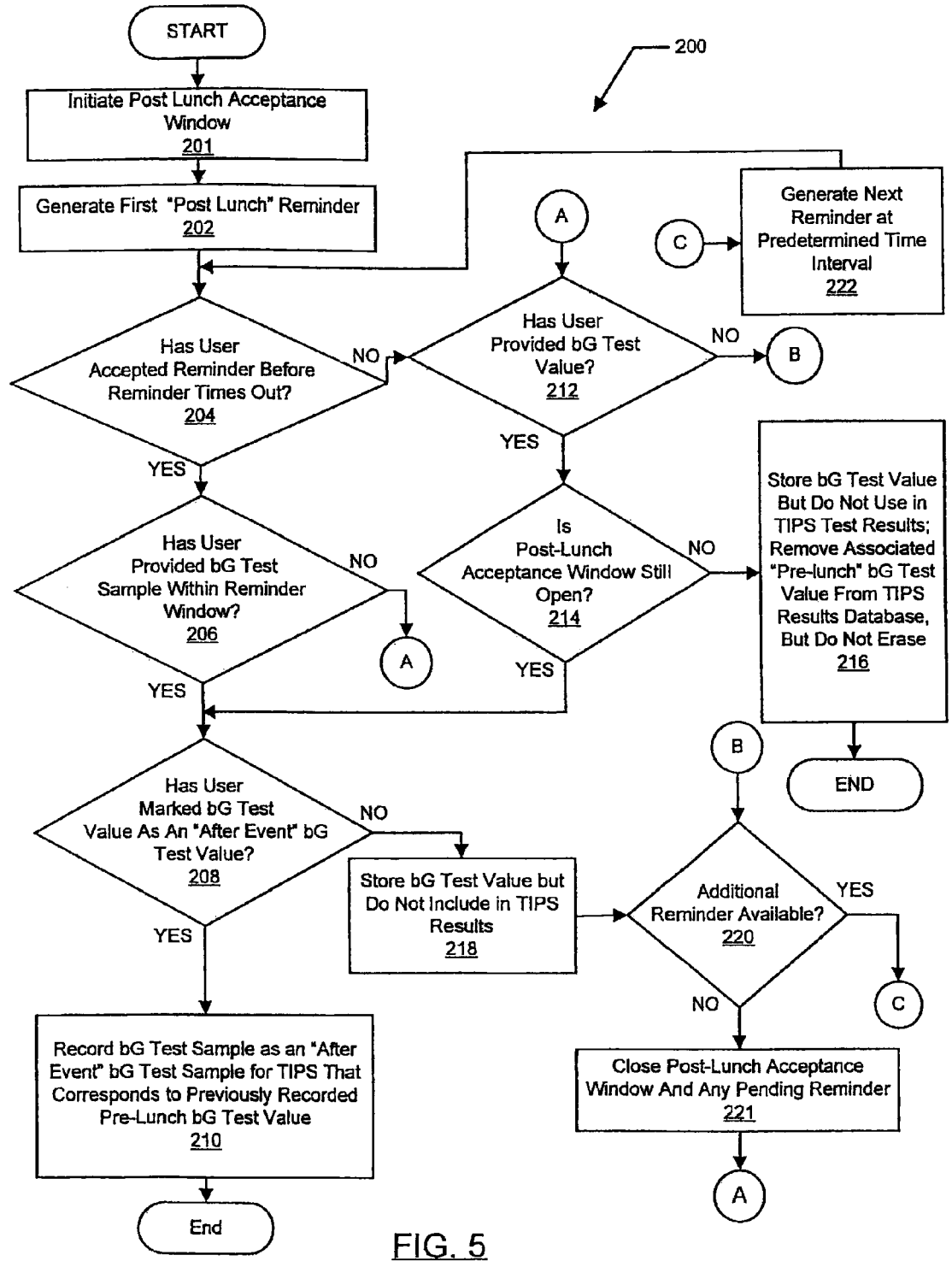
FIG. 5 is an exemplary flowchart of operations that can be performed with the device of FIG. 1 in obtaining a Post-lunch bG test value.

Referring now to FIG. 5, a flowchart 200 is shown for operations that can be performed in obtaining a Post-lunch bG value. It will be noted that flowchart 200 is similar in its sequence of operations to flowchart 100 of FIG. 4. At operation 202 the "Post Lunch" acceptance time window is opened and the first "Post-lunch" reminder is generated. At operation 204 a check is made by the processing subsystem 22 to determine if the user has responded to the reminder before it times out. If the user has responded, then a check is made at operation 206 to determine if the user has obtained a time stamped bG test value within the reminder window. If the user has obtained such a bG test value, then a check is made at operation 208 to determine if the user has marked the bG test value as an "After" event bG test value. If so, the bG test value is stored and used in the TIPs test to form the second one of a pair of bG test values for the Lunch event, as indicated at operation 210. The Post-Lunch acceptance window and any pending Post-Lunch reminders are closed.

If the check at operation 204 reveals that the current reminder window has timed out, then a check is made at operation 212 to determine if the user has provided a bG test value. If so, then a check is made at operation 214 to determine if the current acceptance time window is still open. If so, then operation 208 is repeated. If the check at operation 214 reveals that the current acceptance window has closed, then the previously recorded bG test value (corresponding to the Pre-Lunch bG test) is deleted from the database 26 where the TIPs results are being collected, as indicated at operation 216, but the just-recorded bG test value otherwise remains stored in the database 26. If the check at operation 208 reveals that the user has obtained, a bG test value but has not marked it as an "After" event bG test value, then it can be stored in the database 26, as indicated at operation 218, but it will not be used for the TIPs results. A check will then be made at operation 220 to see if any additional reminders are available to be presented to the user and, if so, then the next reminder is generated at operation 222. If no additional reminder is available, then at operation 221 the Post-lunch acceptance window and any pending reminder are closed, and operation 212 is then repeated. If the check at operation 212 reveals that the user has not provided a bG test value after accepting a reminder, then operation 220 can be repeated.

Figure 6A:
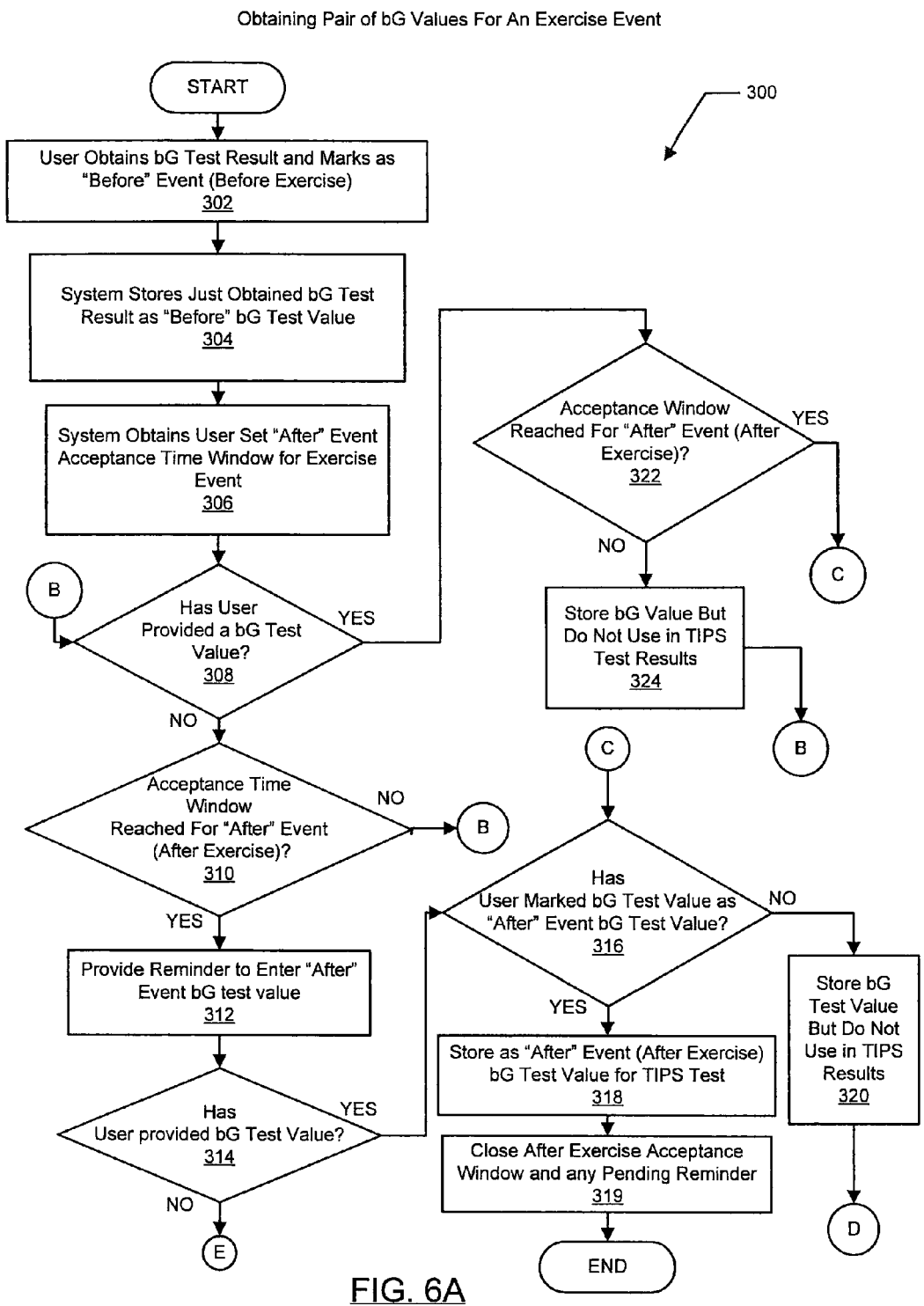
FIGS. 6A and 6B show an exemplary flowchart of operations that can be performed with the device of FIG. 1 in obtaining an "Exercise" bG test value and a Post-exercise bG test value, for the purpose of collecting data for the TIPs test.
Figure 6B:
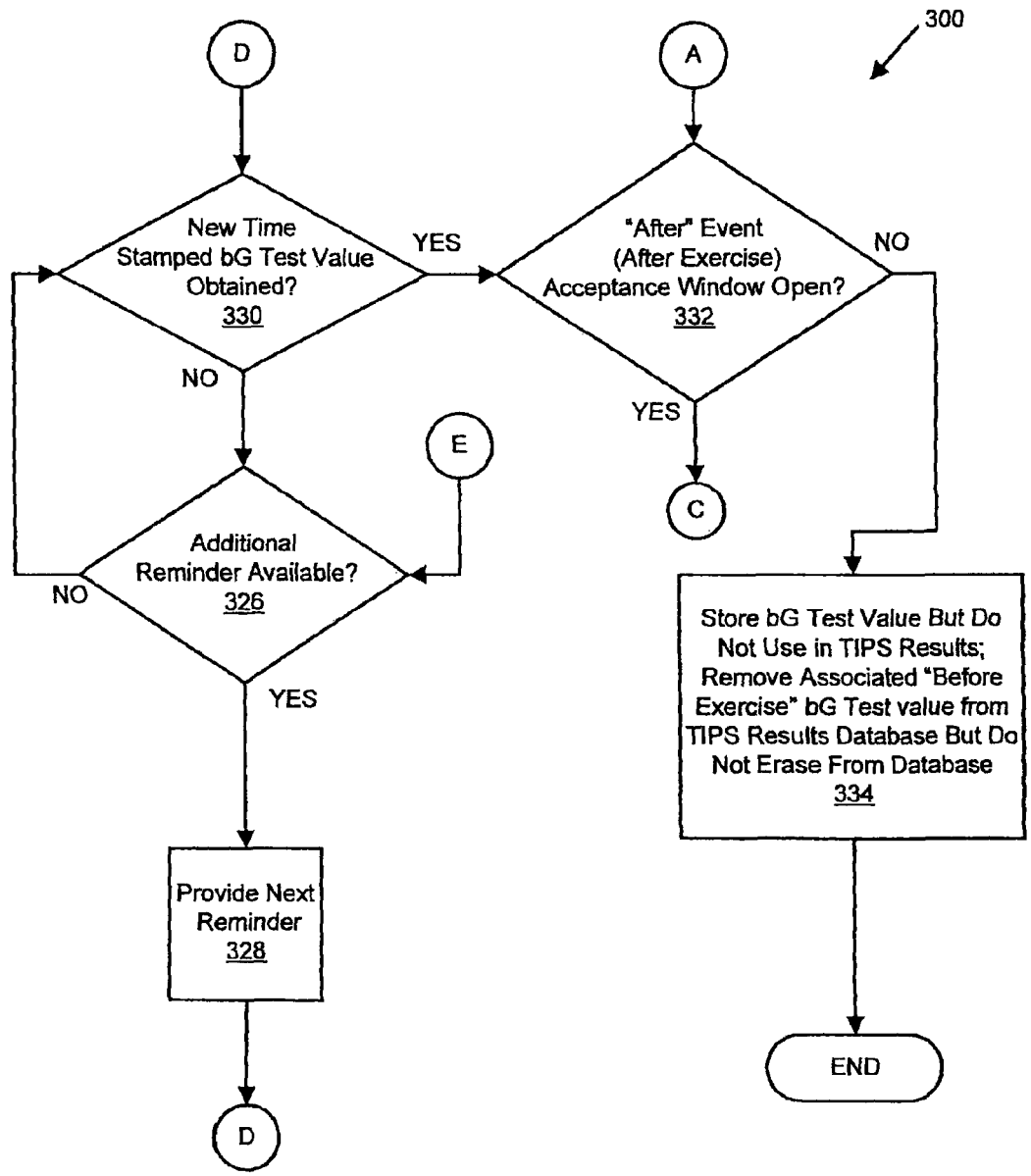

Referring now to FIGS. 6A and 6B, an exemplary flowchart 300 for obtaining an Exercise bG pair for the TIPs test is shown. At operation 302 the user can obtain a bG test value before an exercise event, and labels the test value as a "Before Exercise" event. At operation 304 the device 10 stores the just-obtained bG test value as a Before Event value. At operation 306 the processing subsystem 22 obtains the user set acceptance time window for an "After Exercise" event. The processing subsystem 22 then checks if the user has provided a bG test value, as indicated at operation 308. If not, then a check is made if the acceptance time for the Exercise "After" event is now open, as indicated at operation 310. If the check at operation 310 returns a "Yes" answer, then the first reminder is provided to the user to enter the "After" event bG test value, as indicated at operation 312. A check is then made to determine if the user has provided a bG test value, as indicated at operation 314. If the answer is "Yes", then a check is made to determine if the user has marked the bG test value as an "After" event bG test value, as indicated at operation 316. If the answer is "Yes", then the bG test value is stored in the database 26 as the "After" event bG test value, as indicated at operation 318, and used in the TIPs test results. The After exercise acceptance time window and any pending reminder are then closed, as indicated at operation 319. If the check at operation 316 returns a "No" answer, then the bG test value is stored in the database 26, as indicated at operation 320, but it will not be included in the TIPs test results.

If the check at operation 314 reveals that the user did not provide a response to the first reminder, then a check is made if an additional reminder is available to be provided, as indicated at operation 326 (FIG. 6B). If the check at operation 326 indicates that another reminder is available, then at operation 328 the next reminder is provided to the user at the predetermined reminder time interval.

If the check at operation 326 indicates that no additional reminders are available to be provided, then a check is made at operation 330 to determine if the user has entered a new time stamped bG test value. If not, then operation 326 is repeated. If so, then a check is made to see if the "After" event acceptance time window is still open, as indicated at operation 332. If the "After" event acceptance time window is no longer open, then the bG test value can be stored in the database but will not be included in the TIPs results, as indicated at operation 334. The associated "Before" event bG test value will also be removed from the TIPs results but will not be erased from the database 26. If the check at operation 332 reveals that the acceptance time window is still open, then operation 316 (FIG. 6A) can be repeated.

Figure 7A:
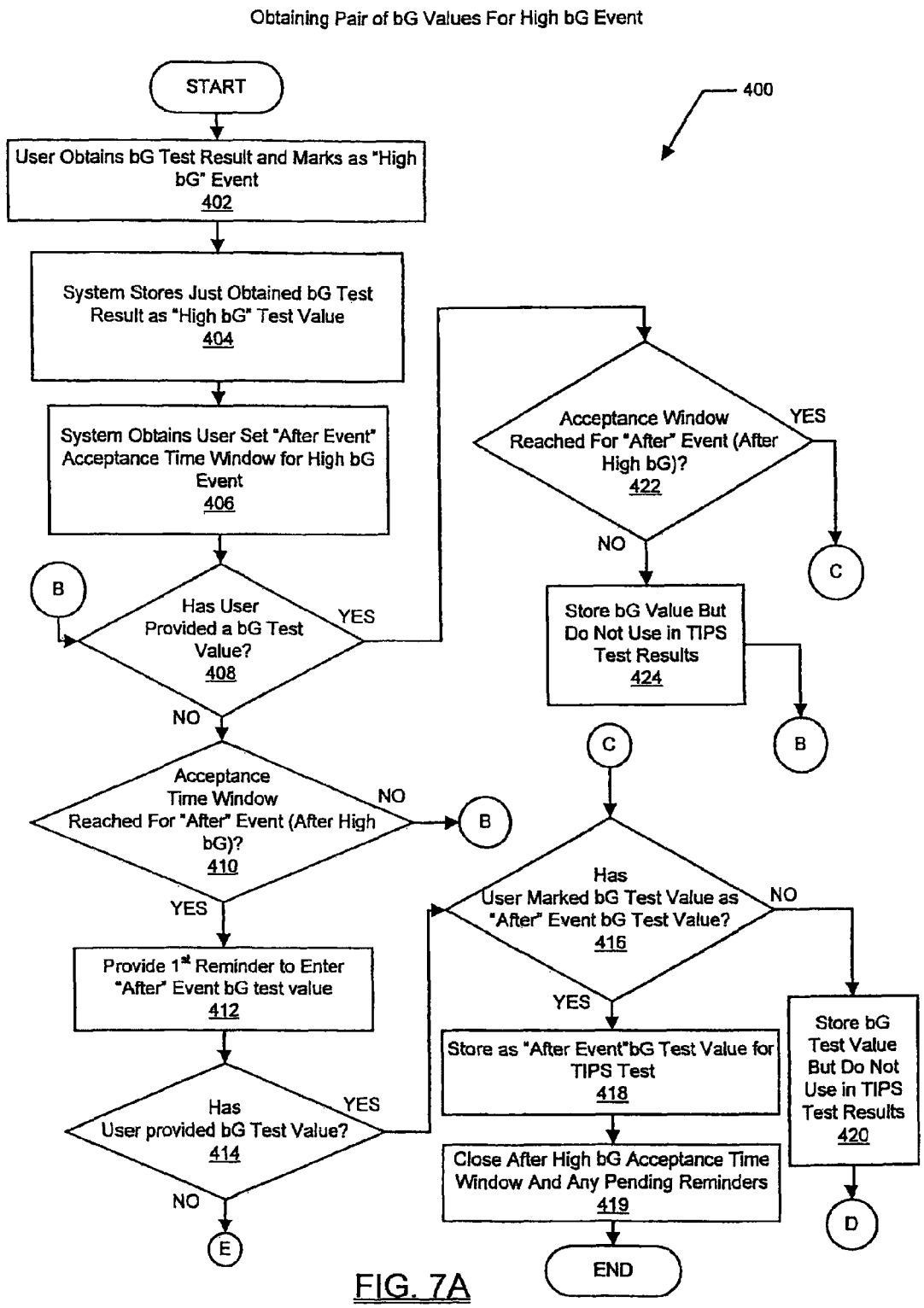
FIGS. 7A and 7B show an exemplary flowchart of operations that can be performed with the device of FIG. 1 in obtaining a High bG pair of test values for the TIPs test.
Figure 7B:
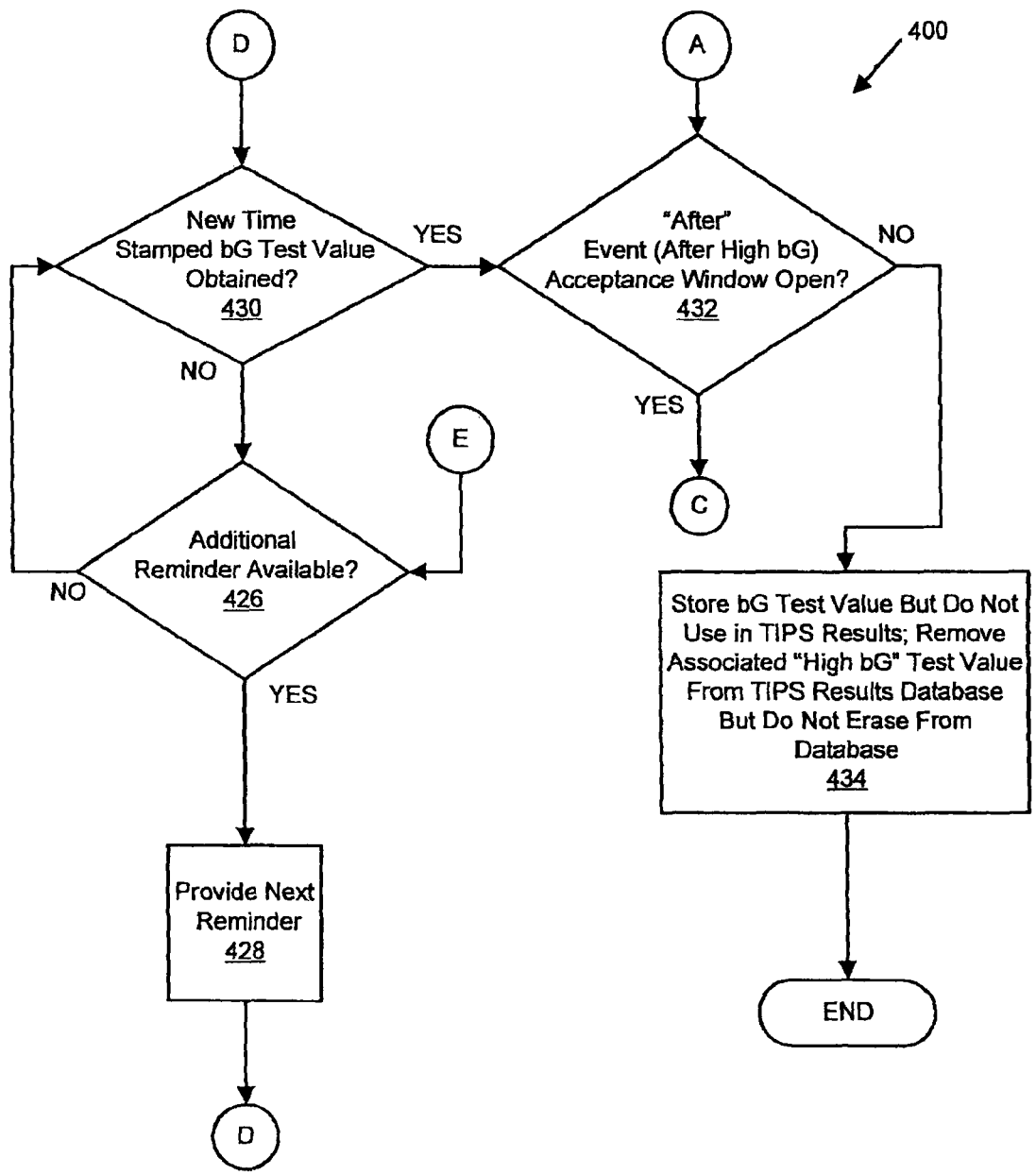

At FIGS. 7A and 7B a flowchart 400 is shown for the operations that can be implemented in recording a pair of bG test values for a "High bG" event. It will be noted that operations 402-434 of this flowchart are similar to those for the "Exercise" event described in connection with FIGS. 6A and 6B. At operation 402 the user obtains a "High bG" test result, which can be automatically recognized by the processing subsystem 22 when reading a time stamped bG test value from the bG analyzer 24. By "automatically recognized" it is meant that once the TIPs test is initiated by the user, the software module 22a will automatically be monitoring for a "High bG" event as well as a "Low bG" event. When the user obtains a time stamped bG value that falls above or below the pertinent bG threshold for triggering either the "High bG" event or the "Low bG" event, this will be detected by the software module 22a. In this example the "High bG" TIPs test is initiated and the corresponding event is detected. The processing subsystem 22 will then store the just-obtained bG test value in the database 26 as the first one of a related pair of bG test values for the "High bG" event, as indicated at operation 404. At operation 406 the "After" event acceptance time window for the "High bG" event is obtained. The remaining operations 408-434 parallel those explained above for FIGS. 6A and 6B, and therefore the description of these operations will not be repeated. If a Low bG TIPs test is initiated, obtaining a pair of bG test values for a "Low bG" event involves essentially the same sequence of operations as that described above for a "High bG" event, with the exception being that the processing subsystem 22 automatically detects a Low bG time stamped value instead of a high bG time stamped value.

Various exemplary set up times and acceptance reminder windows for different Events are illustrated in the chart of FIG. 8. FIG. 9 illustrates a data structure showing how multiple different types of structured tests can be recorded/monitored by the device 10. In this example "ST#" indicates two structured tests are recorded, with the first one (001) being still in progress, while the second one (002) has completed. The "Status" field may indicate, in addition to "IN PROGRESS" and "COMPLETE", a notation for "SCHEDULED", which indicates that a structured test has been scheduled into the device 10 but not yet initiated. The notation "CANCELLED" may also appear, which means that the structured test was cancelled by the user before its completion.

FIG. 10 illustrates how the accumulated data for a single structured test may be stored in a record in the database 26. In this example the "SAMPLE" column contains numbers "1" and "2" that both correspond to "GROUP" "1", meaning that these samples form the first pair of the TIPs results. The "NOTES" field contains any notes entered by the user when the user marked the related bG test value with a marker.

A TIPs test can be considered completed after a predetermined number of related pairs of bG test values have been obtained. It is expected that for most users obtaining seven related pairs of bG test values can suffice to complete a TIPs test, although optimum results would likely involve obtaining seven related pairs of bG test values for seven consecutive days. When initially configuring the variables for the TIPs test, the user could be provided with an option to select how many pairs of bG test values are to be obtained for the TIPs test and then the processing subsystem 22 can signal the user when the required number of related pairs of bG test values has been obtained. If the user skips entering an "After" event bG test value (e.g., Post-lunch) that corresponds to a previously entered bG test value, and instead enters a another subsequent "Before" event bG test value (e.g., Pre-Dinner), the previously marked "Before" event bG test value should be marked "Incomplete" for purposes of the TIPs results, and ignored in presenting the test results to the user. It is also preferred that the software module 22a display a field where the user can select from different options involving one or more of "Medication", "Food", "Exercise", "Health", "Insulin". By selecting one or more of these options, the user can correlate additional information to the event for which he/she is marking a bG test sample. For example, by selecting "Food", the user can be presented with various carbohydrate quantity options to select from that identify the level of carbohydrates that were consumed at a given meal event that the user is marking a time stamped bG test value during the TIPs test.

The system and method of the present disclosure provides a highly desirable device 10 and method of operation by which related pairs of bG test values can be collected and recorded for future use by the user or a health care professional in studying events (including diet and lifestyle) affecting the user, and how such events impact the user's bG levels. The device 10 can enable the TIPs results to be displayed on the display 16 in chart form, in graphical form, or in any other manner that is helpful to the user in understanding the changes in bG levels for different events and/or in response to different types (or quantities) of foods consumed at given meals. If the display 16 is a color touchscreen display, then various colors could be used to highlight various ones of the bG test values, such as those corresponding to High bG or Low bG events. The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same can also be varied in many ways. Such variations are not to be regarded as a departure from the disclosure, and all such modifications are intended to be included within the scope of the disclosure.

In one aspect the present disclosure relates to a method for conducting a Testing In Pairs (TIPs) blood glucose (bG) test using a handheld diabetes management device carried by a user. The method can comprise using a processing subsystem to implement a software module for managing the TIPs test. The software module can control the generation of a plurality of predetermined acceptance time windows corresponding to different user defined events. The processing subsystem can be used to identify specific ones of a plurality of bG test values read by the device which are obtained during the predetermined bG acceptance time windows, and which are identified as being related pairs of accepted bG test values that correspond to specific ones of the user defined events. The processing subsystem can be used to store the related pairs of accepted bG test values in a database. The processing subsystem can conclude the TIN test when a predetermined number of pairs of accepted bG test values has been stored in the database and can use the stored bG test values in providing results of the TIPs test to the user. The results of the TIPs test can be provided on a touchscreen display of the device. Furthermore, the bG acceptance time windows can be defined by the user using a touchscreen display of the device. Furthermore, the user defined events comprise at least two of the following group of events: a breakfast meal; a lunch meal; a dinner meal; a bedtime; a low bG test result; a high bG test result; and an exercise event. Moreover, the predetermined bG acceptance windows can include at least two or more of the following bG acceptance time windows: a Breakfast bG acceptance time window; an After-breakfast bG acceptance time window; a Lunch bG acceptance time window; an After-lunch bG acceptance time window; a Dinner bG acceptance time window; an After-dinner bG acceptance time window; a Bedtime bG acceptance window; an After-exercise bG acceptance time window; a Low-bG acceptance time window; and a High-bG acceptance time window. Still further, the predetermined bG acceptance time window can be provided in accordance with user set Post Meal times, where the user set Post Meal times occur after each of user set breakfast, lunch and dinner times. Furthermore, the predetermined bG acceptance time windows can include an After Exercise bG acceptance time window that is provided in accordance with a user set After Exercise time, and where the After Exercise bG acceptance time window begins thirty minutes before the user set After Exercise time and ends thirty minutes after the user set After Exercise time. Moreover, the predetermined bG acceptance time windows can include an After High bG acceptance time window that is provided in accordance with a user set After High bG time, and where the After High bG acceptance time window begins thirty minutes before the user set After High bG time and ends thirty minutes after the user set After High bG time. Furthermore, the predetermined bG acceptance time windows can include an After Low bG acceptance time window that is provided in accordance with a user set After Low bG time, and where the After Low bG acceptance time window begins fifteen minutes before the user set After Low bG time and ends fifteen minutes after the user set After Low bG time. Still further, the processing subsystem can detect the beginning of each one of the bG acceptance time windows and generate a reminder to the user of the device to announce a beginning of each one of the bG acceptance time windows. Still further, the processing subsystem can detect that two ones of the bG acceptance windows are open simultaneously and overlapping, and can signal the user to mark a just obtained bG test result as being preprandial or postprandial.

In another aspect the present disclosure relates to a method for conducting a TIPs test using a handheld diabetes management device carried by a user. The method can comprise using a processing subsystem to implement a software module for managing the TIPs test, the software module controlling the generation of a plurality of predetermined bG acceptance time windows corresponding to different user defined events. A color touchscreen display of the device, which is in communication with the processing subsystem, can be used to enable a user to configure the device to implement the predetermined bG acceptance time windows, to mark bG test values read by the device as preprandial or postprandial bG test values, and to display results of the TIPs test. The processing subsystem can also be used to provide a reminder to the user during each one of the predetermined bG acceptance time windows to perform a bG test and to provide a bG test value for the purpose of carrying out the TIPs test. The processing subsystem can also be used to identify specific ones of a plurality of bG test values read by the device, which are obtained during the predetermined bG acceptance time windows, as being related pairs of accepted bG test values that correspond to specific ones of the user defined events. The user defined events can include a Breakfast event, a Lunch event, a Dinner event, a Low bG event; a High bG event and an Exercise event. The processing subsystem can also store the related pairs of accepted bG test values in a database and can conclude the TIPs test when a predetermined number Of pairs of accepted bG test values have been stored in the database. The processing subsystem can also be used to retrieve and use the accepted bG test values stored in the database and to display the results of the TIPS test to the user. Still further, the predetermined bG acceptance windows can include at least two of the following bG acceptance time windows: a Breakfast bG acceptance time window; an After-breakfast bG acceptance time window; a Lunch bG acceptance time window; an After-lunch bG acceptance time window; a Dinner bG acceptance time window; an After-dinner bG acceptance time window; a Bedtime bG acceptance window; an After-exercise bG acceptance time window; a Low-bG acceptance time window; and a High-bG acceptance time window. Furthermore, the predetermined bG acceptance time windows can include an After High bG acceptance time window that is provided in accordance with a user set After High bG time, and where the After High bG acceptance time window begins thirty minutes before the user set After High bG time and ends thirty minutes after the user set After High bG time. Moreover, the processing subsystem can detect that two ones of the bG acceptance windows are open simultaneously and overlapping, and can signal the user to mark a just obtained bG test result as being preprandial or postprandial.

In still another aspect the present disclosure relates to a handheld diabetes management device for monitoring and recording bG levels of a user. The device can comprise a port for receiving a bG test strip input by a user and a bG analyzer for reading the bG test strip. A software module can be included for conducting a TIPs test using the device. A processing subsystem can be included which is responsive to an output from the bG analyzer and which uses the bG test value provided by the bG analyzer. The processing subsystem can run the software module, with the software module controlling the generation of a plurality of predetermined acceptance time windows corresponding to different user defined events programmed into the software module by the user. The processing system can further be adapted to identify specific ones of a plurality of bG test values read by the device, which are obtained during the predetermined bG acceptance time windows, as being related pairs of accepted bG test values that correspond to specific ones of the user defined events. A database can be in communication with the processing subsystem for storing the related pairs of accepted bG test values. Furthermore, the device can comprise a touchscreen display in communication with the processing subsystem for enabling the user to program the different user defined events into the device. Still further, the touchscreen display can comprise a color touchscreen display, and the user defined events can comprise a breakfast meal, a lunch meal, a dinner meal, a bedtime, a low bG test result, a high bG test result and an exercise event. Furthermore, the predetermined bG acceptance time windows can comprise two or more of a Breakfast bG acceptance time window; an After-breakfast bG acceptance time window; a Lunch bG acceptance time window; an After-lunch bG acceptance time window; a Dinner bG acceptance time window; an After-dinner bG acceptance time window; a Bedtime bG acceptance window; an After-exercise bG acceptance time window; a Low-bG acceptance time window; and a High-bG acceptance time window. Still further, the processing subsystem can detect the beginning of each one of the bG acceptance time windows and can generate a reminder to the user of the device to announce a beginning of each one of the bG acceptance time windows.

A method for conducting a Testing In Pairs (TIPs) blood glucose (bG) test using a handheld diabetes management device carried by a user is also disclosed. The method can comprise using a processing subsystem to implement a software module for managing the TIPs test, the software module controlling the generation of a plurality of predetermined acceptance time windows corresponding to different user defined events. The processing system can be used to identify specific ones of a plurality of bG test values read by the device, which are obtained during said predetermined bG acceptance time windows, as being related pairs of accepted bG test values that correspond to specific ones of the user defined events, the user defined events including; a breakfast meal; a lunch meal; a dinner meal; a bedtime; a low bG test result; and a high bG test result; an exercise event. The predetermined bG acceptance time window; can include: a Breakfast bG acceptance time window; an After-breakfast bG acceptance time window; a Lunch bG acceptance time window; an After-lunch bG acceptance time window; a Dinner bG acceptance time window; an After-dinner bG acceptance time window; a Bedtime bG acceptance window; an After-exercise bG acceptance time window; a Low-bG acceptance time window; and a High-bG acceptance time window.

One skilled in the art will appreciate that the teachings can be practiced with embodiments other than those disclosed. The disclosed embodiments are presented for purposes of illustration and not limitation, and the invention is only limited by the claims that follow.

What is claimed is:

1. A method for conducting a Testing In Pairs (TIPs) blood glucose (bG) test using a handheld diabetes management device carried by a user, the method comprising:
   using a processing subsystem to implement a software module for managing the TIPs test, the software module controlling the generation of a plurality of predetermined acceptance time windows corresponding to different user defined events;
   using the processing system to generate an initial reminder to the user of the device to announce a beginning of a particular one of the acceptance time windows;
   using the processing system to process an input indicating user's intent to enter a bG measure, the input being received in response to the initial reminder;
   using the processing system to determine whether the user has provided bG measure, the determination in response to receiving the input and occurring in a predefined amount of time from the receipt of the input;
   using the processing system to generate another reminder to the user to enter a bG measure in response to a determination that a bG measure was not received in the time since the initial reminder was generated;
   using the processing system to identify related pairs of accepted bG test values from a plurality of bG test values read by the device obtained during said predetermined bG acceptance time windows corresponding to user defined events;
   using the processing subsystem to store the related pairs of accepted bG test values in a database;
   using the processing subsystem to conclude the TIPs test when a predetermined number of related pairs of accepted bG test values have been stored in the database; and
   using the processing subsystem to retrieve and use the related pairs of accepted bG test values stored in the database in providing results of the TIPs test.

2. The method of claim 1, wherein the results of the TIPs test are provided on a touchscreen display of the device.

3. The method of claim 1, wherein the bG acceptance time windows are defined by the user using a touchscreen display of the device.

4. The method of claim 1, wherein the user defined events comprise at least two of the following group of events:
   a breakfast meal;
   a lunch meal;
   a dinner meal;
   a bedtime;
   a low bG test result;
   a high bG test result; and
   an exercise event.

5. The method of claim 1, wherein the predetermined bG acceptance windows include at least two, or more of the following bG acceptance time windows:
   a Breakfast bG acceptance time window;
   an After-breakfast bG acceptance time window;
   a Lunch bG acceptance time window;
   an After-lunch bG acceptance time window;
   a Dinner bG acceptance time window;
   an After-dinner bG acceptance time window; and
   a Bedtime bG acceptance window;
   an After-exercise bG acceptance time window;
   a Low-bG acceptance time window; and
   a High-bG acceptance time window.

6. The method of claim 1, wherein the predetermined bG acceptance time windows are provided in accordance with user set Post Meal times, where the user set Post Meal times occur after each of user set breakfast, lunch and dinner times.

7. The method of claim 1, wherein the predetermined bG acceptance time windows include an After Exercise bG acceptance time window that is provided in accordance with a user set After Exercise time, and where the After Exercise bG acceptance time window begins thirty minutes before the user set After Exercise time and ends thirty minutes after the user set After Exercise time.

8. The method of claim 1, wherein the predetermined bG acceptance time windows include an After High bG acceptance time window that is provided in accordance with a user set After High bG time, and where the After High bG acceptance time window begins thirty minutes before the user set After High bG time and ends thirty minutes after the user set After High bG time.

9. The method of claim 1, wherein the predetermined bG acceptance time windows include an After Low bG acceptance time window that is provided in accordance with a user set After Low bG time, and where the After Low bG acceptance time window begins fifteen minutes before the user set After Low bG time and ends fifteen minutes after the user set After Low bG time.

10. The method of claim 1, wherein the processing subsystem detects that two of the bG acceptance windows are open simultaneously and overlapping, and signals the user to mark a just obtained bG test result as being preprandial or postprandial.

11. A method for conducting a Testing In Pairs (TIPs) blood glucose (bG) test using a handheld diabetes management device carried by a user, the method comprising:
   using a processing subsystem to implement a software module for managing the TIPs test, the software module controlling the generation of a plurality of predetermined bG acceptance time windows corresponding to different user defined events;
   using a color touchscreen display of the device, which is in communication with the processing subsystem, to enable a user to configure the device to implement the predetermined bG acceptance time windows, to mark bG test values read by the device as preprandial or postprandial bG test values, and to display results of the TIPs test;
   using the processing subsystem to provide a reminder to the user during each one of the predetermined bG acceptance time windows, to perform a bG test and to provide a bG test value for the purpose of carrying out the TIPs test;
   using the processing system to process an input indicating user's intent to enter a bG measure, the input being received in response to the initial reminder;
   using the processing system to determine whether the user has provided bG measure, the determination in response to receiving the input and occurring in a predefined amount of time from the receipt of the input;
   using the processing system to generate another reminder to the user to enter a bG measure in response to a determination that a bG measure was not received in the time since the initial reminder was generated;
   using the processing system to identify related pairs of accepted bG test values from a plurality of bG test values read by the device obtained during said predetermined bG acceptance time windows corresponding to user defined events, and where the user defined events include a Breakfast event, a Lunch event, a Dinner event, a Low bG event; a High bG event and an exercise event;
   using the processing subsystem to store the related pairs of bG test values in a database;
   using the processing subsystem to conclude the TIPs test when a predetermined number of related pairs of accepted bG test values have been stored in the database; and
   using the processing subsystem to retrieve and use the related pairs of accepted bG test values stored in the database and to display the results of the TIPs test to the user.

12. The method of claim 11, wherein the predetermined bG acceptance windows include at least two of the following bG acceptance time windows:
   a Breakfast bG acceptance time window;
   an After-breakfast bG acceptance time window;
   a Lunch bG acceptance time window;
   an After-lunch bG acceptance time window;
   a Dinner bG acceptance time window;
   an After-dinner bG acceptance time window; and
   a Bedtime bG acceptance window;
   an After-exercise bG acceptance time window;
   a Low-bG acceptance time window; and
   a High-bG acceptance time window.

13. The method of claim 11, wherein the predetermined bG acceptance time windows include an After High bG acceptance time window that is provided in accordance with a user set After High bG time, and where the After High bG acceptance time window begins thirty minutes before the user set After High bG time and ends thirty minutes after the user set After High bG time.

14. The method of claim 11, wherein the processing subsystem detects that two of the bG acceptance windows are open simultaneously and overlapping, and signals the user to mark a just obtained bG test result as being preprandial or postprandial.

15. A handheld diabetes management device for monitoring and recording blood glucose (bG) levels of a user, the device comprising:
   a port for receiving a bG test strip input by a user;
   a bG analyzer for reading the bG test strip and generating a bG test value;
   a software module for conducting a Testing In Pairs (TIPs) bG test using the device;
   a processing subsystem responsive to an output from the bG analyzer, the processing subsystem further operating to run software module, the software module controlling the generation of a plurality of predetermined acceptance time windows corresponding to different user defined events programmed into the software module by the user;
   the processing system further adapted to identify related pairs of accepted bG test values from a plurality of bG test values read by the device obtained during said predetermined bG acceptance time windows corresponding to user defined events;
   the processing system further adapted to generate an initial reminder to the user of the device to announce a beginning of a particular one of the acceptance time windows and to process an input indicating user's intent to enter a bG measure, the input being received in response to the initial reminder;
   the processing system further adapted to determine whether the user has provided bG measure, the determination in response to receiving the input and occurring in a predefined amount of time from the receipt of the input, and generate another reminder to the user to enter a bG measure in response to a determination that a bG measure was not received in the time since the initial reminder was generated;
   a database in communication with the processing subsystem for storing the related pairs of accepted bG test values.

16. The handheld diabetes management device of claim 15, further comprising a touchscreen display in communication with the processing subsystem for enabling the user to program the different user defined events into the device.

17. The handheld diabetes management device of claim 15, wherein the touchscreen display comprises a color touchscreen display, and wherein the user defined events comprise a breakfast meal, a lunch meal, a dinner meal, a bedtime, a low bG test result, a high bG test result, and an exercise event.

18. The handheld diabetes management device of claim 17, wherein the predetermined bG acceptance time windows comprise two or more of
   a Breakfast bG acceptance time window;
   an After-breakfast bG acceptance time window;
   a Lunch bG acceptance time window;
   an After-lunch bG acceptance time window;
   a Dinner bG acceptance time window;
   an After-dinner bG acceptance time window; and
   a Bedtime bG acceptance window;
   an After-exercise bG acceptance time window;
   a Low-bG acceptance time window; and
   a High-bG acceptance time window.

19. The handheld diabetes management device of claim 18, wherein the processing subsystem detects the beginning of each of the bG acceptance time windows and generates a reminder to the user of the device to announce a beginning of each one of the bG acceptance time windows.

\* \* \* \* \*